United States Patent [19]

Bandi et al.

[11] Patent Number: 4,902,501
[45] Date of Patent: Feb. 20, 1990

[54] PHARMACEUTICAL COMPOSITIONS ENDOWED WITH SEQUESTERING ACTIVITY FOR THE BILIARY ACIDS, CONTAINING COLESTYRAMIN AS THEIR ACTIVE PRINCIPLE, AND PROCESS FOR PREPARING THEM

[75] Inventors: Gianluigi S. Bandi, Milan; Mauro Valenti, Magenta, both of Italy

[73] Assignee: Prodotti Formenti S.r.L., Milan, Italy

[21] Appl. No.: 61,302

[22] Filed: Jun. 12, 1987

[30] Foreign Application Priority Data

Jun. 16, 1986 [IT]  Italy ............................... 20799 A/86

[51] Int. Cl.$^4$ ............................................. A61K 31/74
[52] U.S. Cl. ....................................................... 424/79
[58] Field of Search .................................... 424/78, 79

[56] References Cited

U.S. PATENT DOCUMENTS

| | | | |
|---|---|---|---|
| 2,838,440 | 6/1958 | Thurmon | 424/79 |
| 3,780,171 | 12/1973 | Irmscher et al. | 424/79 |
| 4,340,585 | 7/1982 | Borzatta et al. | 424/79 |

OTHER PUBLICATIONS

Journal of Pediatrics, Apr. 1976, vol. 88. No. 4, Part 1, pp. 659–661.

*Primary Examiner*—Joseph L. Schofer
*Assistant Examiner*—Peter F. Kulkosky
*Attorney, Agent, or Firm*—Cushman, Darby & Cushman

[57] ABSTRACT

The object of the present invention is a pharmaceutical composition for oral usage, endowed with sequestering activity for the biliary acids, containing colestryramin as its active principle, characterized in that it comprises at least one antimicrobial agent, at least one suspending agent and at least one coating agent.

18 Claims, No Drawings

PHARMACEUTICAL COMPOSITIONS ENDOWED WITH SEQUESTERING ACTIVITY FOR THE BILIARY ACIDS, CONTAINING COLESTYRAMIN AS THEIR ACTIVE PRINCIPLE, AND PROCESS FOR PREPARING THEM

The colestyramin is a strong anionic resin containing quaternary ammonium functional groups bonded to a polymeric styrene-divinylbenzene structure.

It was introduced in the therapy in 1959 and is prevailingly used in the management of the hypercholesterolemic states.

The therapeutical activity of colestyramin is correlated to the capability of that resin of sequestering the biliary acids of the intestine, increasing up to 7-8 times the faecal elimination thereof, reducing their haematic level and consequently increasing the metabolization of the endogenous cholesterol necessary for their biosynthesis.

The result is a considerable reduction in the haematic levels of cholesterol.

TENNET et al. (J. Lipid. Res., 1, 469, 1960) have observed that 1 g of colestyramin in 100 ml of water adsorbs 91.4% of a 1% sodium cholate solution.

CAREY and WILLIAMS (JAMA, 5, 432, 1961) have observed that in man, following a daily dosage of 10 g of colestyramin, the faecal level of desoxycholic acid increases from 125 to 980 mg and that the level of the biliary acids in the serum decreases from 11.8–54.6 mcg/cc to 1.6–16.8 mcg/cc.

DATTA and SHERLOCK (World Congress of Gastroenterology, Volume 3, Munch 1962, page 239; and Brit. Med. J., 5325, 216, 1963) report that the reduction in cholemia seems to prevailingly concern cholic acid, i.e., a trihydroxy biliary acid. Besides on the biliary acids, colestyramin performs its activity also on bilirubin.

The hypocholesterolemic activity of colestyramin observed by BERGEN et co-workers (Proc. Soc. Exp. Biol. Med., 102, 676, 1959), and which is probably the basis of the resin's name, was confirmed by many Authors both in experimental biology and in clinics.

TENNET observed this phenomenon on dogs, VAN ITALLIE (New Engl. J. Med., 265, 469, 1961; and Med. Clin. N. Am. 47, 629, 1963) observed it in the primitive biliary cirrhoses.

A detailed study was carried out by VISINTINE et co-workers (Lancet, 2, 341, 1961) on the behaviour of the lipemia in a subject with biliary cirrhosis treated with colestyramin.

Further evidences on the clinic usage and on the activity of colestyramin are cited by W. H. JOHNS and T. R. BATES (J. Phar. Sci., 1969, 58, 179); and S. LINDENBAUM and T. HIGUCHI (J. Phar. Sci., 1975, 64, 1887).

It must be observed however that, although colestyramin is indicated as the election treatment of pure hypercholesterolemiae, its long-term usage is limited by its poor tolerability and palatability.

Presently, all the preparations based on colestyramin available from the market, or anyway described by the medical literature, belong to the class of the solid pharmaceutical forms to be dispersed in water before the administering thereof, and are generally characterized by a poor palatability.

We observe on this regard that the known process of industrial synthesis of colestyramin provides the polymerization of styrene and divinylbenzene, and the following functionalization of the polymer with quaternary ammonium groups.

The end product from the synthesis is a slurry (an aqueous suspension) of gelular colestyramin constituted by microspheres of about 1 mm of diameter, and with a water content ranging from 40 to 80%.

The colestyramin powder, suitable for use in the pharmaceutical field and complying with the specification of U.S. Pharm. XXIst, is obtained by grinding and drying the slurry. The so-obtained powder is constituted by granules of dimensions of from 5 to 200 microns, has a water content lower than 12%, and can be used for the preparation of solid pharmaceutical forms for extemporaneous administration.

On this regard, it should be observed that the therapeutically efficacious dosis of the presently used preparates of colestyramin powder to be suspended at use time is generally fixed around 12 g daily, and that the administration of such preparate can furthermore cause negative side effects, above all, constipation.

Thus, it would be desirable, and this is a purpose of the present invention, to be able to reduce the therapeutically efficacious dosage of colestyramin, both to enable the manufacturer to attain an economic advantage in terms of the used amount of active principle, and to reduce the side effects which such an active principle can cause on the patient.

A further purpose of the present invention is of providing pharmaceutically acceptable preparations of colestyramin carried and stabilized in suspension in an aqueous carrier, by starting, as the starting material, both from gelular spheroidal colestyramin, and from colestyramin powder; according to the invention, it is desired that such new compositions of colestyramin are endowed with optimum properties of tolerability and palatability.

A purpose of the invention is also that of obtaining the perfect preservation over time of the chemical-physical and microbiological characteristics of the suspension of colestyramin which has to be produced.

According to the purposes of the invention, such stabilized colestyramin suspension must constitute the starting point from which in an advantageous way suitably formulated, ready for use, liquid pharmaceutical forms can be derived.

According to a further purpose, the suspension which the invention wants to provide can be also submitted to drying, so to obtain a powder pre-formulate, from which solid pharmaceutical forms can be derived.

For the accomplishing of the above stated purposes, the present invention purposes a pharmaceutical composition for oral usage, endowed with activity of sequestering of the biliary acids, containing colestyramin as its active principle, characterized in that it comprises at least one antimicrobial agent, at least one suspending agent and at least one coating agent.

The antimicrobial agent(s) which can be used for preparing the colestyramin composition as disclosed above can be selected from the antimicrobial agents having the following characteristics:
they must be widely compatible with colestyramin;
they must show a good chemical-physical stability, and a long-term action capability
they must be efficacious within a pH range of from 2 to 7, and must not alter the pH of the preparations;
they must display a zero or little pharmacological or physiologic activity;

they must be odourless and tasteless;
they must be easily entered in the composition;
they must be free from toxicity.

As a consequence, they can be selected from the following categories:

phenols and phenol derivatives (e.g.: amyl-meta-cresol, chloroxylenol);

esters of p-hydroxybenzoic acid (e.g.: methyl p-hydroxybenzoate, ethyl p-hydroxybenzoate, propyl p-hydroxybenzoate, butyl p-hydroxybenzoate, benzyl p-hydroxybenzoate);

chlorinated aromatic and aliphatic alcohols (e.g.: benzyl alcohol, phenylethyl alcohol, phenoxyethyl alcohol, chlorobutanol, 4-chlorobenzyl alcohol, 2,4-dichlorobenzyl alcohol, 4-chloro-β-phenylethyl alcohol);

aromatic and aliphatic carboxy acids (e.g.: benzoic acid, sorbic acid).

The selection of the suspending and coating agents can be carried out from the following categories:

polymers from animal sources (e.g.: gelatin of swine and bovine type, lactalbumin, ovalbumin, milk protein hydrolysates, casein hydrolysates);

polymers of vegetable origin (e.g.: agar, gum arabic, guar gum, gum tragacanth, galactomannan, pectin, alginates and derivatives, cellulose and derivatives, starchs and derivatives);

suspending agents of synthetic origin (e.g.: polyvinylpyrrolidone, polyvinylpyrrolidone/vinyl acetate, polyvinyl alcohol, cellulose esters).

For the preparation of a composition according to the invention, the process can be performed as follows:

(a) An aqueous solution is prepared, which contains both the antimicrobial agents and the suspending agents to be used. The total concentration of the solution of the antimicrobial agents must be comprised within the range of from 0.05 to 0.35%, preferably of from 0.1 to 0.30%. The amount of the suspending agents is related to the chemical-physical characteristics of the suspending agent(s) used; in any case, it can range from 1 to 10% weight/weight (w/w).

(b) According to the product used as the starting material, the second manufacturing step consists in the preparation of a suspension, or slurry, of colestyramin in water. In case gelular spheroidal colestyramin is used, the resin content of the slurry must be comprised within the range of from 20 to 40% w/w, preferably of from 25 to 35% w/w, and the dimension of the microspheres must be comprised within the range of from 0.25 to 1.5 mm, preferably of from 0.5 to 1 mm. In case, on the contrary, the process is started from powder colestyramin, the dimensions of the granules must be comprised within the range of from 5 to 200 microns, preferably of from 50 to 150 microns. The colestyramin, having the above-cited characteristics, is suspended in purified water, so to obtain a slurry having a colestyramin concentration comprised within the range of from 5 to 25% w/w, preferably of from 10 to 22.5%, ideally of from 12.5 to 20%. For the purpose of better suspending possible clots of colestyramin, fast mixing systems can be used, or the suspension can undergo a homogenization by a turbine or a high-speed turboemulsifier, operating, e.g., at 3,000 r.p.m.

(c) To the colestyramin suspension prepared at point (b) the solution containing the antimicrobial and the suspending agents is added with vigorous stirring. In case, on the contrary, gelular spheroidal colestyramin was used, it is this latter which is added to the solution of the antimicrobial agents. The addition rate must be adjusted as a function of the stirring capacity of the system used, and depends also on the concentration of the starting colestyramin slurry. At the end of the addition, the stirring is continued until a homogeneous suspension is obtained.

(d) At this point, in case as the starting material the slurry of gelular spheroidal colestyramin was used, the suspension obtained at point (c) undergoes a process of granulometric reduction-normalization by means of a colloidal mill, which regularizes the dimensions of the particles within a range of from 5 to 200 microns, preferably of from 50 to 150 microns. In case, on the contrary, as the starting material a colestyramin powder having the above-mentioned granulometric characteristics was used, the suspension undergoes a further homogenization by means of a rotary-head homogenizer. In both cases, the end target is that of obtaining a homogeneous dispersion of the antimicrobial agent around each colestyramin particle. The same holds true for the suspending agent. In general, as relates to the functionalized-chain natural polymers, as it occurs in case of polypeptides, wherein amino groups ($NH_2$) and acidic groups (COOH) are present at the same time, under suitable pH conditions it is possible to cause the coating agents to homogeneously distribute on the colestyramin particles, with the result that the organoleptic characteristics are improved, the agglomeration is prevented, and the fast re-suspension is made possible of the preparates at the usage time.

(e) The stabilized suspension can be used as the starting material for the preparation of the liquid pharmaceutical forms, or it can undergo a drying by the spray dry system, and the resulting powder can be used for the preparation of solid pharmaceutical forms.

For the purpose of better understanding characteristics and advantages of the invention, hereunder examples are disclosed of practical embodiment, which in no way must be considered as being limitative of the same invention.

EXAMPLE 1

The colestyramin used as the starting material: A slurry of gelular microporous colestyramin having the following characteristics:

| | |
|---|---|
| Appearance: | Semi-solid agglomerate constituted by microspheres |
| Colour: | Translucid with light yellow reflexes |
| Smell: | Odourless |
| Suspension pH: | 5.0 |
| Dry Residue | 28% |
| Exchange Capacity: (computed relatively to the dry substance and expressed as g of sodium glycocholate per resin g) | 1.9 g/g |
| Chlorides: (computed relatively to the dry substance) | 13.2% |
| Ashes: (computed relatively to the dry substance) | 0.01% |
| Heavy Metals: (computed relatively to the dry substance) | Less than 0.002% |
| Dialysable Quaternary Amines: | 0.01% |

-continued

| | |
|---|---|
| (computed relatively to the dry substance) | |
| Trimethylamine: (computed relatively to the dry substance) | 13 p.p.m. |
| Particle Dimension: | 35% comprised within the range of from 0.6 to 1 mm |
| Total Microbial Count: | 20/g |
| Mildews, Yeasts and Choliforms: | None |

The Antimicrobial Agent: a mixture of Paracombin ® and Prevan ® (FORMENTI registered trademarks) was used.

The useable combinations of Paracombin and Prevan are comprised within the range of from 1:100 to 100:1 w/w.

In this specific example, an equal-weight mixture of the two antimicrobial agents was used, which was in accordance with the following percent chemical composition:

| | |
|---|---|
| Sodium dehydroacetate | 50.00 |
| Methyl p-hydroxybenzoate | 20.00 |
| Ethyl p-hydroxybenzoate | 15.75 |
| Propyl p-hydroxybenzoate | 13.00 |
| Butyl p-hydroxybenzoate | 1.00 |
| Benzyl p-hydroxybenzoate | 0.25 |
| | 100.00 |

The Suspending Agents: a mixture was used of two suspending agents: gum arabic and propyleneglycol alginate in a ratio of about 4:1.

The Qualitative-Quantitative Composition:

| | STANDARD BATCH | % w/w |
|---|---|---|
| Slurry of gelular and microporous colestyramin | kg 1,072 | 47.50 |
| Paracombin-Prevan mixture | kg 6 | 0.266 |
| Gum arabic | kg 30 | 1.328 |
| Propyleneglycol alginate | kg 7 | 0.310 |
| Citric acid | kg 4 | 0.177 |
| Sorbitol | kg 100 | 4.430 |
| Orange aroma | kg 10 | 0.433 |
| Purified water | kg 1,028 | 45.55 |
| | kg 2,257 | |

PREPARATION

1st Step

To a stainless steel-dissolver of 4,000 liters of capacity, provided with a jacket for the steam-heating and the water-cooling, with temperature control system, with a variable-speed stirrer and with a wet-millin device (such as the colloidal mills of FRYMA, SILVERSON, FITZMILL, etc., type may be):

| | | |
|---|---|---|
| Purified water is charged. | kg | 1,028 |

The temperature is increased to 80° C., and, with a vigorous stirring:

| | | |
|---|---|---|
| Paracombin-Prevan mixture | kg | 6 |

-continued

| | | |
|---|---|---|
| is dissolved. | | |

The temperature is maintained, and stirring is continued until the dissolving of the antimicrobial agents is complete.

The temperature is reduced to 50° C. and then:

| | | |
|---|---|---|
| Gum arabic is dissolved. | kg | 30 |

After that the gum has been completely dissolved:

| | | |
|---|---|---|
| Propyleneglycol alginate is added. | kg | 7 |

The stirring is continued until a moderately viscous, clear solution is obtained; the stirring is then adjusted at 700-800 r.p.m., and the temperature is set at the controlled value of 50° C.

2nd Step

With the solution being maintained under the above specified conditions, and with the colloidal mill being set at the milling degree of approximately 0.5 mm, to this solution 1,072 kg (corresponding to 300 kg of gelular anhydrous colestyramin) is fed, by pumping, of a slurry of colestyramin spheroidal particles.

After the addition, the whole mixture is maintained at 40°-50° C., and stirring is continued for about 1 hour; the milling degree of the colloidal milling is then set at 50-150 mm, and the whole homogenizing of the mixture is then waited for.

The temperature is reduced down to 30° C., and then

| | | |
|---|---|---|
| Citric acid powder | kg | 4 | is added, so to stabilize the pH at a value of from 3 to 6.

Instead of citric acid, any else pharmaceutical-grade organic acid, such as tartaric acid, fumaric acid, adipic acid, ascorbic acid, etc., can be used. The formulation is completed by adding to the stabilized colestyramin suspension, sorbital (as a sweetener) and orange aroma (as a flavouring essence).

As relates to the sweeteners, these can be selected from all of the common sweeteners useable in the pharmaceutical field, and which range from common saccharose to mannitol, fructose, saccharin, etc.

Also the used amount is left at the discretion of the desired organoleptic characteristics.

The same holds true for the flavouring essence.

In the case of the above cited example, the following amounts were used:

| | | |
|---|---|---|
| Sorbitol | kg | 100 |
| Orange aroma | kg | 10 |

Finally, the homogenizing is continued for about 1 hour, and the mixture is then cooled down to room temperature.

The so-prepared suspension was submitted to chemical and microbiological analyses.

In particular, as relates to the chemical analysis, the following parameters were taken into consideration:
Appearance of the suspension;
pH of the suspension;
Viscosity;
Specific gravity;
Particle size;
Measurement of the sequestering rate;
Measurement of the exchange capacity.

The results obtained are reported in Table 1.

TABLE 1

| PARAMETERS | RESULTS |
| --- | --- |
| Appearance of the suspension | Homogenous suspension with a light yellow colour, with orange smell |
| pH | 3.5 |
| Viscosity at 25° C. | 300–500 mPascal s. |
| Specific gravity | 1.052 g/ml |
| particle size | 95% comprised within the range of from 50 to 500 microns |
| Sequestering rate | >90% after 5 minutes |
| Exchange capacity | 1.95 g/g |

The determination of the exchange capacity was carried out according to the method as reported in U.S. Pharmacopoeia XXIst, page 214.

For the determination of the sequestering rate, the method as described in U.S. Pharm. was slightly modified, by using sodium cholate instead of sodium glycocholate. In any case, the calibration curve was prepared for sodium cholate; to such curve, reference was made for the computations.

The curve obtained from the sample solutions is comparable to that obtained from the standard solutions; furthermore, the amount of sodium cholate fixed onto the resin during the first 5 minutes of reaction is, in any case, more than 80% of the total amount, As to the organoleptic characteristics, with the colestyramin suspension tests of acceptability and palatability against a solid preparation (single-dose bags) were carried out on 20 volunteers.

For that purpose, single-dose vials were used, which contained an amount of suspension corresponding to 3 g of stabilized and orange-flavoured colestyramin suspension.

All those who took part in the test expressed a favourable opinion on the suspension preparation, both as relates to the organoleptic characteristics, and the palatability as well as to the greater usage practicality thereof.

At the therapeutical level, it must be furthermore reported that the use of the ready-to-use colestyramin suspension enables the patient to better comply with the dosage plan, and finally that it allows a colestyramin to be intaken which, by being already soaked, is already under the best conditions of reactivity for a fast sequestering of the biliary acids.

As to this latter aspect, clinical studies were performed on 20 patients afflicted with primitive hypercholesterolemia, of whom: ten patients were treated 4 weeks long with 9 g daily of colestyramin formulated in suspension as disclosed in the present example, whilst the remaining 10 patients were treated with 12 g daily of a preparate of colestyramin powder to be suspended at the usage time.

The decreases in total cholesterol relatively to the basal values, obtained after a 4-week treatment, were as follows:

| Colestyramin suspension: | 24.6% |
| --- | --- |
| Colestyramin powder: | 28.5% |

The statistic analysis evidenced that no differences existed between the two active treatments, and that both of them caused a meaningful reduction ($p < 0.05\%$) of total cholesterol relatively to the basal values.

In any case, it must be observed that, in as much as between the two results no differences in significance exist, the result obtained by administering 9 g daily of colestyramin suspension allows a better therapeutical efficacy, and hence a lower incidence of side effects.

EXAMPLE 2

The colestyramin used as the starting material: Colestyramin powder complying with the specifications as reported in U.S. Pharm. XXIst, page 214.

The Antimicrobial Agent: Identical to that used in Example 1.

The Suspending Agents: Identical to those used in Example 1.

The Qualitative-Quantitative Composition:

|  | STANDARD BATCH | % w/w |
| --- | --- | --- |
| Anhydrous Colestyramin Powder | kg 300 | 13.29 |
| Paracombin-Prevan mixture | kg 6 | 0.266 |
| Gum arabic | kg 30 | 1.328 |
| Propyleneglycol alginate | kg 7 | 0.310 |
| Citric acid | kg 4 | 0.177 |
| Sorbitol | kg 100 | 4.430 |
| Orange aroma | kg 10 | 0.433 |
| Purified water | kg 1,800 | 79.75 |
|  | kg 2,257 |  |

PREPARATION

1st Step

Same as of Example 1, with the difference that the initial water amount to be used is of 600 kg.

2nd Step

To a stainless steel-dissolver of 4,000 liters of capacity, provided with a jacket for the steam-heating and the water-cooling, with temperature control system, with a variable-speed stirrer and with a wet-disintegration device (such as a FRYMA-type colloidal mill, or any other milling system, as the SILVERSON, FITZ-MILL, etc., systems may be):

| Purified water is charged. | kg 1,200 |
| --- | --- |

The stirring of the mixture is started (at 700–700 r.p.m.), the temperature is increased to, and is kept controlled at, 50° C.

With the above specified conditions being maintained, the colloidal mill, set at the milling degree of 0.15–0.05 mm, is started up, and the addition of

| | | |
|---|---|---|
| Colestyramin powder | kg | 300 | in small portions is started.

On powder addition end, with the above-reported operating conditions being maintained, to this suspension the solution of the antimicrobial and suspending agents as prepared in the 1st Step is fed, by pumping, then the process is continued as disclosed in Example 1.

The colestyramin suspension obtained as disclosed in this example has the same chemical, physical, microbiological and bioavailability characteristics as of the suspension obtained by starting from the colestyramin slurry disclosed in Example 1.

EXAMPLE 3

The colestyramin used as the starting material: A slurry of gelular, microporous colestyramin having the same characteristics as of Example 1, except for the dry residue, which was of 29.5%.

The Antimicrobial Agent: Identical to that used in Example 1.

The Suspending Agents: An equal-weight mixture of gum arabic and gelatin.

The Acidifying Agent: Tartaric acid.

The Sweetener: Fructose.

The flavouring Essence: Cocoa aroma.

The Qualitative-Quantitative Composition:

| | STANDARD BATCH | % w/w |
|---|---|---|
| Slurry of gelular, microporous colestyramin | kg 1,017 | 45.06 |
| Paracombin-Prevan mixture | kg 6 | 0.266 |
| Gum arabic | kg 30 | 1.328 |
| Gelatin | kg 30 | 0.310 |
| Tartaric acid | kg 4 | 0.177 |
| Fructose | kg 100 | 4.430 |
| Cocoa aroma | kg 22 | 0.975 |
| Purified water | kg 1,048 | 46.43 |
| | kg 2,257 | |

PREPARATION

Identical to that as disclosed in Example 1.

The colestyramin suspension obtained as disclosed in this example has the same chemical, physical, microbiological and bioavailability characteristics as of the suspension obtained by starting from the colestyramin slurry as disclosed in Example 1.

EXAMPLE 4

The colestyramin used as the starting material: Colestyramin powder complying with the specifications as reported in U.S. Pharm. XXIst, page 214.

The Antimicrobial Agent: A 1:2 w/w mixture was used of amyl-meta-cresol and 2,4-dichlorobenzyl alcohol, which shows a good preserving activity both as relates bacteria and yeasts and mildews.

The Suspending Agents: Gum arabic.

The Coating Agent: The typical characteristic was exploited of the aminoacids, to get fixed, under suitable pH conditions, on the colestyramin structure.

In particular, by using albumin, lactalbumin, milk proteins, casein or soy protein hydrolysates, in slightly alkaline solutions, the co-precipitation can be easily caused of these polypeptides on the particles of colestyramin maintained in suspension, with a microencapsulated colestyramin endowed with optimum characteristics of palatalibiliy being obtained.

In this specific example, an ovalbumin was used, which had the following characteristics:

Humidity: 8% maximum
Protein: 81%
pH: 8.0%
total microbial count: less than 10,000/g
Choliforms: absent/0.1 g
Salmonellae: absent/20 g The Qualitative-Quantitative Composition:

| | STANDARD BATCH | % w/w |
|---|---|---|
| Anhydrous colestyramin powder | kg 60 | 7.83 |
| Amyl-metacresol | kg 0.075 | 0.01 |
| 2,4-Dichlorobenzyl alcohol | kg 0.150 | 0.02 |
| Polyoxyethylenated castor oil | kg 1.500 | 0.2 |
| Ovalbumin | kg 9 | 1.17 |
| Gum arabic | kg 3 | 0.39 |
| Citric acid | kg 0.200 | 0.03 |
| Saccharin sodium | kg 0.500 | 0.065 |
| Orange aroma | kg 2.0 | 0.26 |
| Purified water | kg 690 | 90.03 |
| | kg 766.425 | |

PREPARATION

1st Step

To a stainless-steel dissolver of 2,000 liters of capacity, equipped with a variable-speed stirrer, and with a temperature control unit,

| | | |
|---|---|---|
| Purified water | kg | 90 | is charged, and the temperature is set at the controlled value of 50° C.

Separately, inside a suitable vessel, the antimicrobial agents are dissolved in polyoxyethenated castor oil.

The resulting solution is added, with stirring, to the purified water.

Then, 0.5 kg of saccharin sodium and 9 kg of ovalbumin are added.

The stirring is continued until a clear solution is obtained, and the pH is subsequently adjusted to 8.0–8.5 with 1N sodium hydroxide.

2nd Step

To a stainless-steel dissolver of approximately 1,000 liters of capacity, equipped with a variable-speed stirrer (800–1,500 r.p.m.), 600 kg of purified water is charged, and, with stirring, 60 kg of colestyramin powder, computed as anhydrous substance, is suspended.

Stirring is continued until a homogeneous suspension is obtained.

The pH is adjusted to neutrality with 1N sodium hydroxide.

To this suspension, maintained at about 1,200 r.p.m., the solution prepared in the 1st Step is added: thus, the co-precipitation is obtained of ovalbumin on the colestyramin particles maintained in suspension.

The formulation is then completed with the addition of gum arabic, citric acid and orange aroma.

The colestyramin suspension obtained as disclosed in this example has the same chemical-physical, microbiological and bioavailability characteristics as of the suspension obtained by starting from the colestyramin slurry as disclosed in Example 1.

EXAMPLE 5

To the suspension of coated colestyramin, prepared according to the method as disclosed in Example 4, 0.1% was added of a non-ionic surfactant selected from the non-ionic surfactants commonly used in the pharmaceutical technique and allowed for oral usage (e.g., polysorbate 20).

The resulting suspension was then submitted to a drying by a spray-dry technique in a NIRO-type atomizer.

The powder obtained, constituted by colestyramin coated with ovalbumin and by the co-formulating constituents used in Example 4, can be used for preparing dry oral pharmaceutical forms for extemporaneous administration, or for the preparation of solid pharmaceutical forms (tablets, capsules, etc.) in general.

EXAMPLE 6

The colestyramin used as the starting material: Colestyramin powder complying with U.S. Pharm. XXIst, page 214.
The Antimicrobial Agent: Identical to that used in Example 4.
The Suspending Agents: identical to that used in Example 4.
The Coating Agent: Milk proteins.
The Qualitative-Quantitative Composition:

|  | STANDARD BATCH | % w/w |
|---|---|---|
| Anhydrous colestyramin powder | kg 60 | 7.83 |
| Amyl-metacresol | kg 0.075 | 0.01 |
| 2,4-Dichlorobenzyl alcohol | kg 0.150 | 0.02 |
| Polyoxyethylenated castor oil | kg 1.500 | 0.2 |
| Milk proteins | kg 9 | 1.17 |
| Gum arabic | kg 3 | 0.39 |
| Tartaric acid | kg 0.200 | 0.026 |
| Aspartame | kg 1 | 13.05 |
| Coffee aroma | kg 2 | 0.26 |
| Purified water | kg 690 | 90.03 |
|  | kg 766.425 |  |

PREPARATION

Identical to as disclosed in Examples 4 and 5.

From the above specifications, and from the examples, it can be concluded that in general the advantages deriving from the present invention are essentially the following:

The process of suspension manufacturing is extremely simple and easy and fast to be carried out.

The equipment necessary for the manufacturing is of known type, and easily available from those normally used in the pharmaceutical field.

The useable antimicrobial agents, the suspending agents, the coating agents and the other components used (acidifiers, sweeteners, flavouring essences) are easily available.

All the preparation steps are carried out in the aqueous phase, with the complete exclusion of organic solvents, even of those normally acceptable in the pharmaceutical field, and due to this reason no particular prevention systems are required, such as explosion-proof or pollution-preventing systems.

The present invention enables providing liquid pharmaceutical forms as ready-to-use suspensions wherein the colestyramin is present in an optimum soaking state, a necessary condition for being capable of performing the action of sequestering of the biliary acids.

Furthermore, in case of dry forms, the fact of coating the colestyramin with extremely water-soluble polypeptides makes it possible the optimum soaking of the resin, as well as the fast action of sequestering of the biliary acids, to immediately take place at the time of water re-suspension of the coated colestyramin.

The stabilization technique, which too is an object of the present invention, ensures the maintenance overtime of the characteristics of microbiological purity of the colestyramin, an essential condition for the administering of an oral preparate.

The same techniques of stabilization, which allows, among others, the molecules of polymeric nature of the suspending agent to be microdispersed around the colestyramin particles, inhibits the agglomeration process which would otherways occur due to the effects of the spontaneous decantation of the same particles, and therefore favours the fast re-suspension by simple shaking.

The pharmaceutical forms which can be obtained by the application of the present invention are endowed with optimum organoleptic characteristics in terms of palatability and acceptability.

Such organoleptic characteristics enable furthermore the users to better comply with the individual dosage plan, which, as known, in this type of therapy must be pursued over long time periods (from 4 to 8 weeks) and by repeated cycles.

The use of the composition of the invention allows the therapeutically efficacious daily dosage to be reduced by approximately 25%.

We claim:

1. A pharmaceutical composition for oral administration at improved and reduced therapeutically efficacious dosage levels of cholestyramine said composition possessing sequestering activity of the biliary acids, and comprising colestyramin particles around each of said particles is a homogeneous dispersion of an antimicrobial agent and a suspending or coating agent, said antimicrobial agent being present in an amount ranging from 0.001 to 0.05 gram per gram of colestyramin and said suspending or coating agent being present in an amount ranging from 0.01 to 10 grams per gram of colestyramin.

2. The pharmaceutical composition of claim 1 wherein said antimicrobial agent is selected from the group consisting of a phenol and a derivative thereof, an ester of p-hydroxybenzoic acid, a chlorinated aromatic alcohol, a chlorinated aliphatic alcohol, an aromatic carboxy acid, an aliphatic carboxy acid and sodium dehydroacetate.

3. The pharmaceutical composition of claim 2 wherein said antimicrobial agent is selected from the group consisting of amyl metacresol, chloroxylenol, methyl p-hydroxybenzoate, ethyl p-hydroxybenzoate, propyl p-hydroxybenzoate, butyl p-hydroxybenzoate, benzyl p-hydroxybenzoate, benzyl alcohol, phenylethyl alcohol, phenoxyethyl alcohol, chlorobutanol, 4-chlorobenzyl alcohol, 2,4-dichlorobenzyl alcohol, 4-chloro-β-phenylethyl alcohol, benzoic acid and sorbic acid.

4. The pharmaceutical composition of claim 1 wherein said antimicrobial agent comprises a mixture of sodium dehydroacetate, methyl p-hydroxybenzoate, ethyl p-hydroxybenzoate, propyl p-hydroxybenzoate, butyl p-hydroxybenzoate and benzyl p-hydroxybenzoate.

5. The pharmaceutical composition of claim 4 wherein said antimicrobial agent is present in an amount ranging from 0.05 to 0.35 percent.

6. The pharmaceutical composition of claim 1 wherein said antimicrobial agent comprises a mixture of amyl-metacresol and 2,4-dichlorobenzyl alcohol.

7. The pharmaceutical composition of claim 1 wherein said suspending or coating agent is selected from the group consisting of a polymer from an animal source, a polymer from a vegetable source and a synthetic suspending agent.

8. The pharmaceutical composition of claim 7 wherein said polymer from an animal source is swine gelatin, bovine gelatin, lactalbumin, ovalbumin, milk protein hydrolyzate, casein hydrolyzate, polypeptide and milk protein.

9. The pharmaceutical composition of claim 7 wherein said polymer of vegetable origin is agar, gum arabic, guar gum, gum tragacanth, galactomannan, pectin, alginate, propylene glycol alginate, cellulose, cellulose derivative, starch and starch derivative.

10. The pharmaceutical composition of claim 7 wherein said synthetic suspending agent is polyvinylpyrrolidone, copolymer of polyvinylpyrrolidone and vinyl acetate, polyvinyl alcohol and a cellulose ester.

11. The pharmaceutical composition of claim 7 wherein said suspending or coating agent is a mixture of gum arabic and propyleneglycol alginate.

12. The pharmaceutical composition of claim 9 wherein said polymer of vegetable origin is gum arabic present in an amount ranging from 1 to 3.5% weight/weight.

13. The pharmaceutical composition of claim 9 wherein said polymer of vegetable origin is propyleneglycol alginate present in an amount ranging from 0.1 to 1% weight/weight.

14. The pharmaceutical composition of claim 7 wherein said suspending or coating agent is a polymer from an animal source in an alkaline solution having a pH higher than 7.0.

15. The pharmaceutical composition of claim 1 in the form of an aqueous suspension.

16. The pharmaceutical composition of claim 1 in dry powder form.

17. A process for the preparation of the pharmaceutical composition of claim 1 comprising
   (a) preparing an aqueous solution of said antimicrobial and suspending or coating agents,
   (b) preparing an aqueous slurry or colestyramin starting with gelular spheroidal colestyramin or colestyramin powder,
   (c) mixing the solution resulting from (a) with the slurry resulting from (b) until a homogeneous suspension is obtained, and
   (d) further homogenizing or granulometrically reducing the suspension resulting from (c) until a stabilized suspension is obtained.

18. The process of claim 17 which includes drying the stabilized suspension obtained in step (d).

* * * * *